(12) United States Patent
Murai et al.

(10) Patent No.: US 8,716,709 B2
(45) Date of Patent: May 6, 2014

(54) DISPLAY DEVICE

(75) Inventors: Atsuhito Murai, Osaka (JP); Yoshiharu Kataoka, Osaka (JP); Takuya Watanabe, Osaka (JP); Yuhko Hisada, Osaka (JP); Satoshi Horiuchi, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 13/701,117

(22) PCT Filed: May 18, 2011

(86) PCT No.: PCT/JP2011/061384
§ 371 (c)(1),
(2), (4) Date: Dec. 7, 2012

(87) PCT Pub. No.: WO2011/152210
PCT Pub. Date: Dec. 8, 2011

(65) Prior Publication Data
US 2013/0200373 A1    Aug. 8, 2013

(30) Foreign Application Priority Data

Jun. 3, 2010    (JP) ................. 2010-128166

(51) Int. Cl.
*G01N 27/414*    (2006.01)
*H01L 23/64*    (2006.01)
*H01L 31/08*    (2006.01)

(52) U.S. Cl.
USPC ....... 257/48; 257/429; 257/253; 257/E29.128

(58) Field of Classification Search
None
See application file for complete search history.

(56) References Cited

U.S. PATENT DOCUMENTS

| | | | |
|---|---|---|---|
| 4,056,772 A * | 11/1977 | Graf von Berckheim | 324/72 |
| 4,061,476 A | 12/1977 | Hölter et al. | |
| 4,123,502 A | 10/1978 | Hölter et al. | |
| 4,201,751 A | 5/1980 | Holter et al. | |
| 4,206,186 A | 6/1980 | Hölter et al. | |
| 6,331,706 B1 * | 12/2001 | Orr et al. | 250/385.1 |
| 6,768,311 B2 * | 7/2004 | Aiki et al. | 324/464 |
| 2002/0157950 A1 * | 10/2002 | Frerichs | 204/416 |
| 2003/0001584 A1 * | 1/2003 | Aiki et al. | 324/464 |
| 2003/0006778 A1 * | 1/2003 | Aiki et al. | 324/464 |

(Continued)

FOREIGN PATENT DOCUMENTS

| | | |
|---|---|---|
| JP | 51-113692 A | 10/1976 |
| JP | 2003-336872 A | 11/2003 |
| JP | 2004-156855 A | 6/2004 |

OTHER PUBLICATIONS

International Preliminary Report on Patentability for PCT/JP2011/061384 issued Jan. 8, 2013.*

(Continued)

*Primary Examiner* — Thomas L Dickey
*Assistant Examiner* — Joseph Schoenholtz
(74) *Attorney, Agent, or Firm* — Keating & Bennett, LLP (57) ABSTRACT

The present invention provides an inexpensive display device that includes an ion sensor portion and a display and that can be miniaturized. The present invention is a display device that includes an ion sensor portion including an ion sensor circuit and a display including a display-driving circuit. The display device has a substrate, and at least one portion of the ion sensor circuit and at least one portion of the display-driving circuit are formed on the same main surface of the substrate.

9 Claims, 6 Drawing Sheets

(56) References Cited

U.S. PATENT DOCUMENTS

| | | | |
|---|---|---|---|
| 2006/0035400 A1* | 2/2006 | Wu et al. | 438/49 |
| 2009/0032695 A1* | 2/2009 | Kaye et al. | 250/281 |
| 2011/0100810 A1* | 5/2011 | Merz | 204/406 |
| 2013/0069121 A1* | 3/2013 | Murai et al. | 257/253 |

OTHER PUBLICATIONS

Air Ion Counter data sheet downloaded from URL< http://www.trifield.com/content/air-ion-counted> on Aug. 21, 2013.*

Brown, R.C. "Tutorial Review: Simultaneous Measurement of Particle Size and Particle Charge" Journal of Aerosol Science, vol. 28, No. 8, (1997) pp. 1373-1391.*

Official Communication issued in International Patent Application No. PCT/JP2011/061384, mailed on Jul. 19, 2011.

Murai et al, "Ion Sensor and Display Device", U.S. Appl. No. 13/701,112, filed Nov. 30, 2012.

Murai et al, "Ion Sensor and Display Device", U.S. Appl. No. 13/701,123, filed Nov. 30, 2012.

Murai et al, "Ion Sensor, Display Device, Method for Driving Ion Sensor, and Method for Calculating Ion Concentration", U.S. Appl. No. 13/701,129, filed Nov. 30, 2012.

* cited by examiner

DISPLAY DEVICE

TECHNICAL FIELD

The present invention relates to a display device. More particularly, the present invention relates to a display device that includes an ion sensor portion.

BACKGROUND ART

In recent years, an action has been found that sterilizes bacteria floating in the air using positive ions and negative ions that are generated in the air to thereby make the air clean. Ion generating apparatuses such as air cleaners that apply this technology are attracting significant attention as apparatuses that favorably answer the needs of the modern comfort and health-oriented era.

However, because ions are invisible, their existence cannot be verified by direct sight. On the other hand, it is natural for a user of an air cleaner or the like to want to know whether or not ions are being generated normally, and whether ions of a desired concentration are being generated.

Therefore, an ion generating element that can easily determine the amount of ions and a remote control for an electric home appliance with a built-in ion sensor and the like have been disclosed as ion sensors that measure an ion concentration in the atmosphere. More specifically, an ion generating element that is equipped with an ion sensor portion that determines the amount of positive ions and negative ions generated from an ion generation portion, and a display that displays a determined ion amount is known (for example, see Patent Literature 1). In addition, a remote control for an electric home appliance with a built-in ion sensor is known that includes an ion sensor that measures an ion concentration in the atmosphere and a display that displays the current state of the electric home appliance (for example, see Patent Literature 2).

CITATION LIST

Patent Literature

Patent Literature 1: JP 2003-336872 A
Patent Literature 2: JP 2004-156855 A

SUMMARY OF INVENTION

Technical Problem

Figure 9:
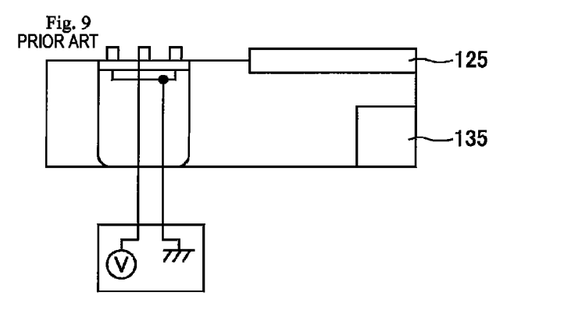
FIG. 9 is a schematic view that illustrates a conventional ion generating element.

However, as shown in FIG. 9, in the ion generating element described in Patent Literature 1, an ion sensor portion 125 and a display 135 are formed separately. That is, the ion sensor portion 125 and the display 135 are formed by respective different processes using respective different materials. Consequently, there is room for improvement in the respect that miniaturization of the ion generating element is difficult and the manufacturing cost is high.

Figure 10:
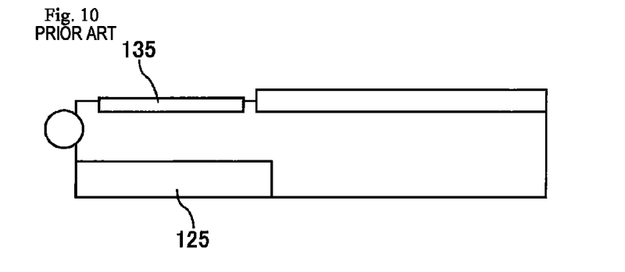
FIG. 10 is a schematic cross-sectional view that shows a cross section of a conventional remote control for an electric home appliance with a built-in ion sensor.

Likewise, in the remote control for an electric home appliance with a built-in ion sensor described in Patent Literature 2, as shown in FIG. 10, an ion sensor portion 125 and a display 135 are formed separately.

When the inventors examined the size of an ion sensor provided in a conventional ion generating apparatus, the inventors found that the ion sensor was constituted by several capacitors, several resistances, one operational amplifier, one connector, an antenna pad, a printed wiring board (PWB) and the like, and that an area occupied by the ion sensor was approximately 15 mm×45 mm, of which an area occupied by the antenna pad was approximately 10 mm×10 mm. Thus, the inventors found that the conventional ion sensor portion is a comparatively large size on the order of millimeters.

The present invention has been made in view of the above described current state of the art, and an object of the present invention is to provide an inexpensive display device that includes an ion sensor portion and a display and that can be miniaturized.

Solution to Problem

The inventors conducted various studies regarding an inexpensive device that includes an ion sensor portion and a display and that can be miniaturized, and focused attention on utilization of a display device that includes at least one substrate, such as a liquid crystal display device. The inventors found that the high cost of conventional devices is due to the fact that an ion sensor and a display are formed separately. Further, the inventors found that by providing at least one portion of an ion sensor circuit that is included in an ion sensor portion and at least one portion of a display-driving circuit that is included in a display on the same main surface of a substrate, the ion sensor circuit can be provided in an empty space such as a picture-frame region of the substrate, and the ion sensor circuit can be formed utilizing a process that forms the display-driving circuit. Having realized that this idea can beautifully solve the above problem, the inventors have arrived at the present invention.

More specifically, one aspect of the present invention provides a display device that includes an ion sensor portion including: an ion sensor circuit; a display including a display-driving circuit; and a substrate, wherein at least one portion of the ion sensor circuit and at least one portion of the display-driving circuit are formed on the same main surface of the substrate.

The display device is described in detail hereinafter.

Although the kind of the display device is not particularly limited, a flat panel display (FPD) may be mentioned as a suitable example thereof. A liquid crystal display device, an organic EL (electro-luminescence) display, and a plasma display may be mentioned as examples of an FPD.

The ion sensor portion includes an element for measuring an ion concentration in air and, in addition to the ion sensor circuit, for example, includes a fan or a lead-in path or the like for introducing ions into the ion sensor circuit. The ion sensor circuit includes at least an element (preferably a field effect transistor (hereinafter, also referred to as "FET") and an ion sensor antenna) that is required for converting an ion concentration in air into an electrical physical quantity, and also includes a function that detects (captures) ions. More specifically, preferably the ion sensor portion includes an ion sensor element, and the at least one portion of the ion sensor circuit is the ion sensor element.

Note that the term "ion sensor element" refers to the minimum required element for converting an ion concentration in air into an electrical physical quantity.

The display includes elements for performing the display functions, and includes, for example, display elements and optical films in addition to the display-driving circuit. The display-driving circuit is a circuit for driving the display elements, and includes, for example, circuits such as a TFT array, a gate driver, and a source driver. Particularly, a TFT array is preferably used as the at least one portion of the display-driving circuit.

The display element has a light-emitting function or light-controlling function (shutter function for light), and is provided for each pixel or sub-pixel of the display device.

For example, a liquid crystal display device usually includes a pair of substrates, and has display elements having a light-controlling function between the substrates. More specifically, the display elements of the liquid crystal display device each usually include a pair of electrodes, and liquid crystals placed between the substrates.

An organic electroluminescence display usually has display elements having a light-emitting function on a substrate. More specifically, the display elements of the organic EL display each usually have a structure in which an anode, an organic electroluminescence layer, and a cathode are stacked.

A plasma display usually has a pair of substrates facing each other, and display elements having a light-emitting function which are placed between the substrates. More specifically, the light-emitting elements of the plasma display usually include a pair of electrodes; a fluorescent material formed on one of the substrates; and rare gas enclosed between the substrates.

The display device having the above components as its essential components is not particularly limited by other components.

Preferred embodiments of the display device are described in detail below.

Preferably the ion sensor circuit includes a first field effect transistor (first FET) and an ion sensor antenna, wherein the ion sensor antenna is connected to a gate electrode of the first FET, the display-driving circuit includes a second field effect transistor (second FET), and the first FET, the ion sensor antenna and the second FET are formed on the same main surface of the substrate. Thus, ions in air can be detected (captured) by the ion sensor antenna, and a current or voltage value between a source and a drain of the first FET can be varied in accordance with the amount of ions detected by the ion sensor antenna. That is, the first FET and ion sensor antenna can be caused to function as an ion sensor element. Further, it is possible to make at least part of the materials and processes for forming the first FET included in the ion sensor element and the second FET the same, and it is thereby possible to reduce the costs required for forming the first FET and second FET. Thus, the ion sensor antenna is a conductive member that detects (captures) ions in air. Consequently, when ions arrive at the ion sensor antenna, the surface of the ion sensor antenna is charged by the ions, and the potential of the gate electrode of the first FET that is connected to the ion sensor antenna changes. As a result, the electric resistance of the channel of the first FET changes.

Further, in the conventional apparatuses that include an ion sensor portion and a display, generally the ion sensor portion utilizes parallel-plate type electrodes. For example, the ion sensor portion described in Patent Literature 1 includes a flat-plate type accelerating electrode and capturing electrode that face each other. In this kind of parallel-plate type ion sensor portion, miniaturization is difficult since processing on the order of micrometers is difficult because of limitations in the processing accuracy in manufacturing. In the remote control for an electric home appliance with a built-in ion sensor described in Patent Literature 2 also, parallel-plate electrodes that are constituted by a set of an ion accelerating electrode and an ion capturing electrode are used in the ion sensor portion, and likewise, miniaturization thereof is difficult. In contrast, by utilizing an FET and an ion sensor antenna as an ion sensor element as described in the above configuration, since it is possible to manufacture the ion sensor element by photolithography, processing on the order of micrometers is enabled, and it is also possible to perform miniaturization to a greater degree than the case of a parallel-plate type ion sensor. Further, an electrode gap (gap between a TFT array substrate and an opposed substrate) is generally between approximately 3 and 5 μm in a liquid crystal display panel, and it is considered difficult to introduce ions into such a gap even when a parallel-plate type ion sensor is formed by providing an electrode on each of the TFT array substrate and the opposed substrate. In contrast, since an ion sensor element that utilizes an FET and an antenna as in the above described configuration does not require an opposed substrate, it is possible to miniaturize a display device that includes the ion sensor.

Although the kind of the first FET and the second FET are not particularly limited, a thin film transistor (hereinafter, also referred to as "TFT") is preferable. A TFT is favorably used in an organic EL display device or liquid crystal display device that employs the active matrix driving method.

Note that, the semiconductor material is not particularly limited, and amorphous silicon (a-Si), polysilicon (p-Si), microcrystalline silicon (μc-Si), continuous grain silicon (CG-Si), and oxide semiconductors may be mentioned as examples thereof.

Preferably, the ion sensor antenna has a surface (exposed portion) that includes a transparent conductive film. In other words, preferably the surface of the ion sensor antenna is covered by the transparent conductive film. A transparent conductive film is highly resistant to corrosion, and therefore an unexposed portion (for example, a portion that includes metal lines) of the ion sensor antenna can be prevented from being exposed to the external environment and corroding.

The transparent conductive film is the first transparent conductive film, and the display preferably includes the second transparent conductive film. Since the transparent conductive film has conductivity and optical transparency, the second transparent conductive film can be suitable for use as a transparent electrode of the display. Also, at least part of the materials and processes for the first transparent conductive film and the second transparent conductive film can be the same. Accordingly, the first transparent conductive film can be formed at a low cost.

The first transparent conductive film and the second transparent conductive film preferably contain the same material(s), and more preferably consist only of the same material(s). Such a structure enables to form the first transparent conductive film at a low cost.

The material of each of the first transparent conductive film and the second transparent conductive film may be any material. For example, indium tin oxide (ITO), indium zinc oxide (IZO), zinc oxide (ZnO), and fluorine-doped tin oxide (FTO) are suitable.

The first FET preferably includes a semiconductor whose properties are changed by light, and the semiconductor is preferably shielded from light by a light-shielding film. Examples of the semiconductor whose properties are changed by light include a-Si and μc-Si. In order to use these semiconductors for an ion sensor, the light is preferably blocked such that the properties do not change. Shielding, from light, the semiconductor whose properties are changed by light enables suitable use of the semiconductor not only for a display but also for an ion sensor portion.

The light-shielding film shields the first FET from light outside the display device (external light) and/or light inside the display device. Examples of the light inside the display device include reflected light produced inside the display device. In the case that the display device is a spontaneous light emission display device such as an organic EL display and a plasma display, examples of the light inside the display device include light emitted from the light-emitting elements provided in the display device. Meanwhile, in the case of a non-spontaneous light emission liquid crystal display device, examples of the light inside the display device include light from the backlight. The reflected light produced inside the display device is about several tens of lux, and the influence on the first FET is comparatively small. Examples of the external light include sunlight and interior illumination (e.g., fluorescent lamp). The sunlight is 3000 to 100000 Lx, and the interior fluorescent lamp at the time of actual use (except for use in a dark room) is 100 to 3000 Lx. Both lights greatly influence the first FET. The light-shielding film preferably shields the first FET from at least the external light, and more preferably blocks both the external light and the light inside the display device.

Preferably, the light-shielding film is the first light-shielding film, and the display has the second light-shielding film. With such a structure, in the case that a liquid crystal display device or an organic EL display is used as the above display device, the second light-shielding film can be provided at borders between the pixels or sub-pixels in the display for prevention of color mixing. Also, at least part of the materials and processes for forming the first light-shielding film and the second light-shielding film can be the same, and therefore the first light-shielding film can be formed at a low cost.

The first light-shielding film and the second light-shielding film preferably contain the same material(s), and more preferably consist only of the same material(s). The first light-shielding film therefore can be formed at a low cost.

Preferably, the ion sensor antenna does not overlap with the channel region of the first FET. Since an ion sensor antenna normally does not include a semiconductor whose properties are changed by light, it is not necessary to shield the ion sensor antenna from light. That is, even if the necessity arises to shield the first FET from light, it is not necessary to provide a light-shielding film around the ion sensor antenna. Accordingly, if the ion sensor antenna is provided outside the channel region as in the above described configuration, the installation location of the ion sensor antenna can be freely decided without being constrained by the installation location of the first FET. Consequently, it is possible to easily form an ion antenna at a location at which ions can be detected more effectively such as, for example, a location that is close to a flow channel or a fan for guiding air to the ion sensor antenna. Although, as described above, a location at which the ion sensor antenna is formed is not particularly limited as long as the ion sensor antenna does not overlap with the channel region of the first FET, preferably the ion sensor antenna is formed inside a lead-in path for introducing ions. Furthermore, it is more preferable to form the ion sensor antenna at a location that is outside the channel region of the first FET and is at an edge part of the substrate rather than in the first FET.

On the other hand, the ion sensor antenna may overlap with the channel region of the first FET. By providing the ion sensor antenna within the channel region in this manner, for example, by adopting a top-gate TFT or a planar TFT as the first FET, the gate electrode of the TFT can itself be caused to function as an ion sensor antenna. Thus, the ion sensor element can be miniaturized further.

At least one portion of the ion sensor circuit and at least one portion of the display-driving circuit are preferably connected to a common power supply. With use of a common power supply, the cost for forming the power supply and the arrangement space for the power supply can be reduced compared to the structure in which the ion sensor portion and the display have different power supplies. More specifically, at least the source or drain of the first FET and the gates of the TFTs in the TFT array are preferably connected to the common power supply.

Preferably the first FET includes a-Si or μc-Si. By using the comparatively inexpensive a-Si or μc-Si, it is possible to provide an ion sensor that, while having a low manufacturing cost, can detect both ions with high accuracy.

The display device may be used for any product. Suitable examples of the product include non-portable displays such as displays for televisions and personal computers. To such a non-portable display, the ion concentration in the indoor environment in which the display is placed can be displayed. The suitable examples also include portable devices such as cell phones and personal digital assistants (PDAs). With such a product, the ion concentration at various places can be measured easily. The suitable examples further include ion generators provided with a display. Such an ion generator can show on the display the concentration of ions emitted from the ion generator.

Advantageous Effects of Invention

According to the present invention, it is possible to provide a low-cost and miniaturizable display device that includes an ion sensor portion and a display.

DESCRIPTION OF EMBODIMENTS

The present invention will be mentioned in more detail referring to the drawings in the following embodiments, but is not limited to these embodiments.

Embodiment 1

Figure 1:
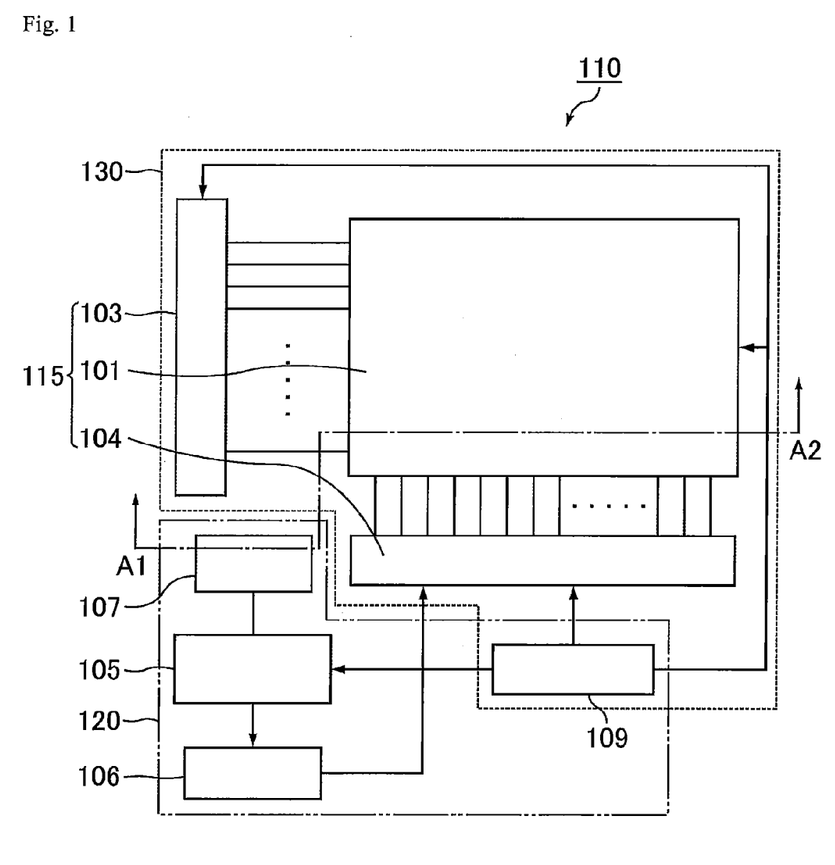
FIG. 1 is a block diagram of a display device according to Embodiments 1 and 2.

The present embodiment is described taking as an example a liquid crystal display device that is equipped with an ion sensor portion for which a detection object is negative ions in air. FIG. 1 is a block diagram of the display device according to the present embodiment.

A display device 110 according to the present embodiment is a liquid crystal display device, and includes an ion sensor portion 120 (ion sensor portion) for measuring the ion concentration in the air, and a display 130 for displaying various images. The display 130 is provided with a display-driving circuit 115 that includes a display-driving TFT array 101, a gate driver (scanning signal line-driving circuit for display) 103, and a source driver (image signal line-driving circuit for display) 104. The ion sensor portion 120 includes an ion sensor driving/reading circuit 105, an arithmetic processing LSI 106, and an ion sensor circuit 107. A power supply circuit 109 is shared by the ion sensor portion 120 and the display 130.

The display 130 has the same circuit structure as a conventional active-matrix display device such as a liquid crystal display device. That is, images are displayed in a region with the TFT array 101 formed, i.e., in a display region, by line sequential driving.

The function of the ion sensor portion 120 is summarized below. First, the negative ions in the air are detected (captured) in the ion sensor circuit 107, and a voltage value corresponding to the detected amount of negative ions is generated. The voltage value is transmitted to the driving/reading circuit 105 where the value is converted into a digital signal. The signal is transmitted to the LSI 106, such that the negative ion concentration is calculated by a certain calculation method, and display data for displaying the calculation result in the display region is generated. The display data is transmitted to the TFT array 101 through a source driver 104, and the negative ion concentration corresponding to the display data is eventually displayed. The power supply circuit 109 supplies electric power to the TFT array 101, the gate driver 103, the source driver 104, and the driving/reading circuit 105. The driving/reading circuit 105 controls the later-described reset line and input line as well as the above functions, and supplies a certain amount of electric power to each line in desired timing.

The driving/reading circuit 105 may be included in another circuit such as the ion sensor circuit 107, the gate driver 103, and the source driver 104, and may be included in the LSI 106.

In the present embodiment, the arithmetic processing may be performed using software that functions on a personal computer (PC) in place of the LSI 106.

Figure 2:
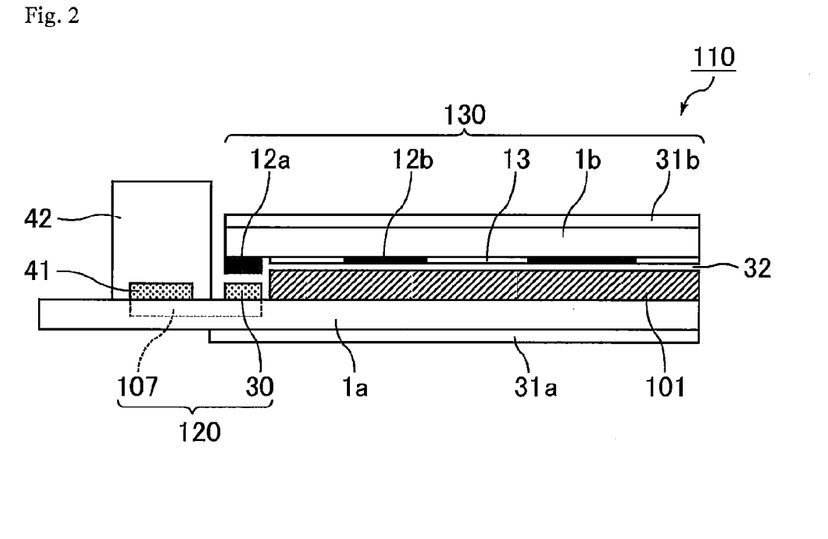
FIG. 2 is a schematic cross-sectional view illustrating a cross section of a display device according to Embodiments 1 and 2.

The structure of the display device 110 is described using FIG. 2. FIG. 2 is a schematic cross-sectional view of the display device which was cut along the line A1-A2 illustrated in FIG. 1. The ion sensor portion 120 is provided with the ion sensor circuit 107, an air ion lead-in/lead-out path 42, a fan (not illustrated), and a light-shielding film 12a (first light-shielding film). The ion sensor circuit 107 contains the ion sensor element that includes a sensor TFT (first FET) 30 and an ion sensor antenna 41. The display 130 is provided with the TFT array 101 including pixel TFTs (second FETs) 40, a light-shielding film 12b (second light-shielding film), a color filter 13 including colors such as RGB and RGBY, liquid crystals 32, and polarizers 31a and 31b.

The antenna 41 is a conductive member for detecting (capturing) negative ions in the air, and is connected to the gate of the sensor TFT 30. The antenna 41 includes a portion to be exposed to the external environment (exposure portion). Negative ions adhering to the surface (exposure portion) of the antenna 41 change the electric potential of the antenna 41, which changes the electric potential of the gate of the sensor TFT 30. As a result, the electric current and/or voltage between the source and drain in the sensor TFT 30 change(s). Thus, an ion sensor element including the antenna 41 and the sensor TFT 30 can be miniaturized compared to the conventional parallel plate ion sensor.

The lead-in/lead-out path 42 is a path for efficiently ventilating the space above the antenna 41. The fan blows air from the observation side to the depth side of FIG. 2, or from the depth side to the observation side.

The display device 110 is provided with two insulating substrates 1a and 1b which face each other in the most part, and the liquid crystals 32 disposed between the substrates 1a and 1b. The sensor TFT 30 and the TFT array 101 are provided on the main surface on the liquid crystal side of the substrate 1a (TFT array substrate) in the region where the substrates 1a and 1b face each other. The TFT array 101 includes pixel TFTs (second FETs) 40 arranged in a matrix state. The antenna 41, lead-in/lead-out path 42, and fan are arranged on the liquid crystal-side main surface of the substrate 1a in the region where the substrates 1a and 1b do not face each other. In this way, the antenna 41 is formed outside the channel regions of the sensor TFT 30. Thereby, the antenna 41 can be easily arranged near the lead-in/lead-out path 42 and the fan, efficiently sending air to the antenna 41. Also, the sensor TFT 30 and the light-shielding film 12a are formed at the end (picture-frame region) of the display 130. The arrangement leads to effective use of the space in the picture-frame region, and therefore the ion sensor circuit 107 can be formed without a change of the size of the display device 110.

On the one same main surface of the substrate 1a, at least the sensor TFT 30 and the ion sensor antenna 41 included in the ion sensor circuit 107, and the TFT array 101 included in the display-driving circuit 115 are formed. Accordingly, the sensor TFT 30 and the ion sensor antenna 41 can be formed using the process of forming the TFT array 101.

The light-shielding films 12a and 12b and the color filter 13 are provided on the liquid crystal-side main surface of the substrate 1b (counter substrate) in the region where the substrates 1a and 1b face each other. The light-shielding film 12a is formed at a position facing the sensor TFT 30, and the light-shielding film 12b and the color filter 13 are formed at a position facing the TFT array 101. The sensor TFT 30 includes a-Si which is a semiconductor whose properties are changed by light, as described in more detail later. Shielding the sensor TFT 30 from light with the light-shielding film 12a enables to reduce the property change of a-Si, i.e., the output property change of the sensor TFT 30. Thereby, the ion concentration can be measured with higher precision.

The polarizers 31a and 31b are formed on the respective main surfaces on the opposite side to the liquid crystals 32 (outer side) of the substrates 1a and 1b.

Figure 3:
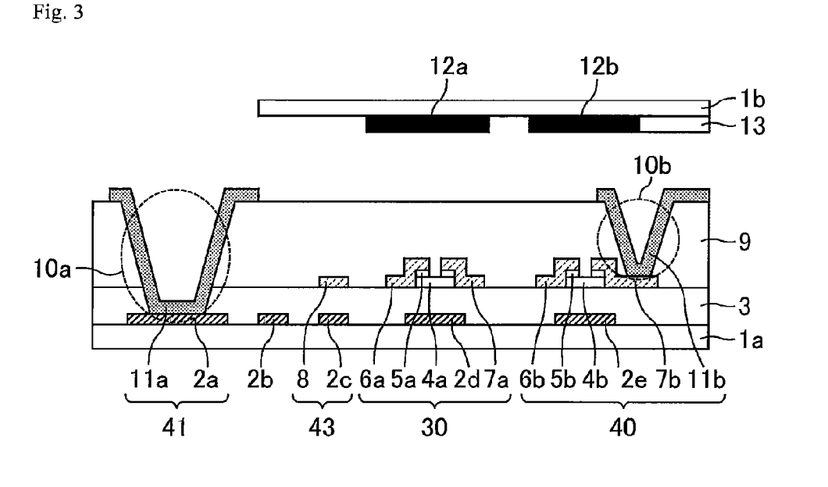
FIG. 3 is a schematic cross-sectional view illustrating a cross section of a display device according to Embodiments 1 and 2.

The structure of the display device 110 is described in more detail with reference to FIG. 3. FIG. 3 is a schematic cross-sectional view of the display device according to the present embodiment.

On the liquid crystal-side main surface of the insulating substrate 1a, a first conductive layer, an insulating film 3, a hydrogenated a-Si layer, an $n^+$ a-Si layer, a second conductive layer, a passivation film 9, and a third conductive layer are stacked in the stated order.

In the first conductive layer, an ion sensor antenna electrode 2a, a reset line 2b, a later-described connection line 22, a node-Z storage capacitor electrode 2c, and gate electrodes 2d and 2e are formed. These electrodes are formed in the first conductive layer, and can be formed by, for example, sputtering and photolithography from the same material through the same process. The first conductive layer is formed from a single or multiple metal layers. Specific examples of the first conductive layer include a single aluminum (Al) layer, a laminate of lower layer of Al/upper layer of titanium (Ti), and a laminate of lower layer of Al/upper layer of molybdenum (Mo). The reset line 2b, the connection line 22, and the storage capacitor electrode 2c are described below in more detail with reference to FIG. 4.

The insulating film 3 is formed on the substrate 1a in such a manner as to cover the ion sensor antenna electrode 2a, the reset line 2b, the connection line 22, the node-Z storage capacitor electrode 2c, and the gate electrodes 2d and 2e. On the insulating film 3, hydrogenated a-Si layers 4a and 4b, $n^+$ a-Si layers 5a and 5b, source electrodes 6a and 6b, drain electrodes 7a and 7b, and a node-Z storage capacitor electrode 8 are formed. The source electrodes 6a and 6b, the drain electrodes 7a and 7b, and the storage capacitor electrode 8 are formed in the second conductive layer, and can be formed by sputtering and photolithography from the same material through the same process. The second conductive layer is formed from a single or multiple metal layers. Specific examples of the second conductive layer include a single aluminum (Al) layer, a laminate of lower layer of Al/upper layer of Ti, and a laminate of lower layer of Ti/upper layer of Al. The hydrogenated a-Si layers 4a and 4b can be formed by, for example, chemical vapor deposition (CVD) and photolithography from the same material through the same process. The $n^+$ a-Si layers 5a and 5b can also be formed by, for example, CVD and photolithography from the same material through the same process. In this way, at least part of the materials and processes can be the same in forming the electrodes and semiconductors. The cost required in formation of the sensor TFT 30 and the pixel TFTs 40 including the electrodes and semiconductors therefore can be reduced. The components of the TFTs 30 and 40 are described in more detail later.

The passivation film 9 is formed on the insulating film 3 in such a manner as to cover the hydrogenated a-Si layers 4a and 4b, $n^+$ a-Si layers 5a and 5b, source electrodes 6a and 6b, drain electrodes 7a and 7b, and storage capacitor electrode 8. On the passivation film 9, a transparent conductive film 11a (first transparent conductive film) and a transparent conductive film 11b (second transparent conductive film) are formed. The transparent conductive film 11a is connected to the antenna electrode 2a via a contact hole 10a that penetrates the insulating film 3 and the passivation film 9. The transparent conductive film 11a is arranged to prevent the antenna electrode 2a from being exposed to the external environment because of the contact hole 10a. Hence, the arrangement makes it possible to prevent corrosion of the antenna electrode 2a as a result of being exposed to the external environment. The transparent conductive film 11b is connected to the drain electrode 7b via a contact hole 10b which penetrates the passivation film 9. These transparent electrodes 11a and 11b are formed in the third conductive layer, and can be formed by, for example, sputtering and photolithography from the same material through the same process. The third conductive layer is formed from a single or multiple transparent conducting films. Specific examples of the transparent conductive films include ITO films and IZO films. The materials constituting the transparent conductive films 11a and 11b are not required to be completely the same as each other. The processes for forming the transparent conductive films 11a and 11b are not required to be completely the same as each other either. For example, in the case that the transparent conductive film 11a and/or the transparent conductive film 11b have/has a multilayer structure, it is also possible to form only layer(s) common to the two transparent conductive films from the same material through the same process. Applying at least part of the materials and processes for forming the transparent conductive film 11b as described above to formation of the transparent conductive film 11a enables to form the transparent conductive film 11a at a low cost.

The light-shielding film 12a and the light-shielding film 12b can also be formed from the same material through the same process. Specifically, the light-shielding films 12a and 12b are formed from opaque metal (e.g. chromium (Cr)) films, opaque resin films, or other films. Examples of the resin films include acrylic resins containing carbon. Applying at least part of the materials and processes for forming the light-shielding film 12b as described above to formation of the light-shielding film 12a enables to form the light-shielding film 12a at a low cost.

The components of the TFTs 30 and 40 are described in more detail. The sensor TFT 30 is formed from the gate electrode 2d, the insulating film 3, the hydrogenated a-Si layer 4a, the $n^+$ a-Si layer 5a, the source electrode 6a, and the drain electrode 7a. The pixel TFTs 40 each are formed from the gate electrode 2e, the insulating film 3, the hydrogenated a-Si layer 4b, the $n^+$ a-Si layer 5b, the source electrode 6b, and the drain electrode 7b. The insulating film 3 functions as a gate insulating film in the sensor TFT 30 and the pixel TFTs 40. The TFTs 30 and 40 are bottom-gate TFTs. The $n^+$ a-Si layers 5a and 5b are doped with a V group element such as phosphorus (P). That is, the sensor TFT 30 and the pixel TFTs 40 are N-channel TFTs.

The antenna 41 is formed from the transparent conductive film 11a and the antenna electrode 2a. Further, a node-Z storage capacitor 43 as a capacitor is formed from the node-Z storage capacitor electrodes 2c and 8 and the insulating film 3 that functions as a dielectric. Since it is possible to increase the capacitance of the gate electrode 2d and the antenna 41 by providing the capacitor 43, the influence of external noise during measurement of an ion concentration can be suppressed. Accordingly, the sensor operations can be made more stable and the accuracy can be further increased.

Figure 4:
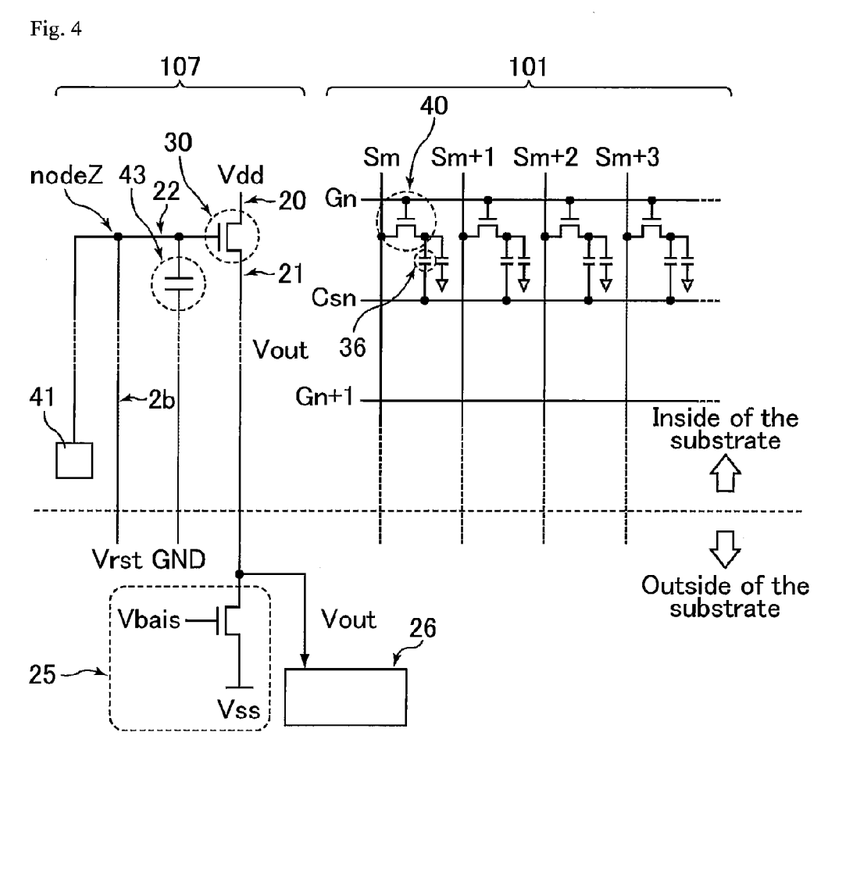
FIG. 4 is an equivalent circuit illustrating an ion sensor circuit 107 and a portion of a TFT array 101 according to Embodiments 1 and 2.

Next, the circuit configuration and the movement mechanism of the ion sensor circuit 107 and the TFT array 101 are described using FIG. 4. FIG. 4 is a view illustrating an equivalent circuit of portions of the ion sensor circuit 107 and the TFT array 101 according to the present embodiment.

First, the TFT array 101 is described. The gate electrodes 2d of the pixel TFTs 40 are connected to the gate driver 103 via the gate bus lines Gn, Gn+1, and so forth. The source electrodes 6b are connected to the source driver 104 via the source bus lines Sm, Sm+1, and so forth. The drain electrodes 7b of the pixel TFTs 40 are connected to the transparent conductive films 11b which function as pixel electrodes. The pixel TFTs 40 are provided in the respective sub-pixels, and function as switching elements. The gate bus lines Gn, Gn+1, and so forth receive scanning pulses (scanning signals) in predetermined timings from the gate driver 103. The scanning pulses are applied to each pixel TFT 40 by a line sequential method. The source bus lines Sm, Sm+1, and so forth receive any image signals provided by the source driver 104 and/or display data calculated based on the negative ion concentration. Then, the image signals and/or display data are/is transmitted, in predetermined timing, to the pixel electrodes (transparent conductive films 11b) connected to the pixel TFTs 40 that are turned on for a certain period by inputted scanning pulses. The image signals and/or display data at a predetermined level written to the liquid crystals are stored for a certain period between the pixel electrodes having received these signals and/or data and the counter electrode (not illustrated) facing the pixel electrodes. Here, together with the liquid crystal capacitors formed between the pixel electrodes and the counter electrode, liquid crystal storage capacitors (Cs) 36 are formed. The liquid crystal storage capacitor 36 is formed between the drain electrode 7a and the liquid crystal auxiliary capacitor line Csn, Csn+1, or the like in the respective sub-pixels. The capacitor lines Csn, Csn+1, and so forth are formed in the first conductive layer, and are disposed in parallel with the gate lines Gn, Gn+1, and so forth.

Next, the circuit configuration of the ion sensor circuit 107 will be described. An input line 20 is connected to the drain electrode 7a of the sensor TFT 30. A high voltage (+10 V) or a low voltage (0 V) is applied to the input line 20, and the voltage of the input line 20 is taken as Vdd. An output line 21 is connected to the source electrode 6a. The voltage of the output line 21 is taken as Vout. Further, the antenna 41 is connected through the connection line 22 to the gate electrode 2d of the sensor TFT 30. The reset line 2b is also connected to the connection line 22. A point of intersection (node) between the lines 22 and 2b is taken as a node-Z. The reset line 2b is a line for resetting the node-Z, that is, a voltage between the gate of the sensor TFT 30 and the antenna 41. A high voltage (+20 V) or a low voltage (−10 V) is applied to the reset line 2b, and the voltage of the reset line 2b is taken as Vrst. In addition, a ground (GND) is connected to the connection line 22 through the storage capacitor 43. A constant current circuit 25 and an analog-digital conversion circuit (ADC) 26 are connected to the output line 21. The constant current circuit 25 is constituted by an N-channel TFT (constant current TFT), and a drain of the constant current TFT is connected to the output line 21. A source of the constant current TFT is connected to a constant current source, and a voltage Vss thereof is fixed to a voltage that is lower than the high voltage of Vdd. A gate of the constant current TFT is connected to a constant voltage source. A voltage Vbais of the gate of the constant current TFT is fixed to a predetermined value so that a constant current (for example, 1 μA) flows between the source and drain of the constant current TFT. The constant current circuit 25 and the ADC 26 are formed inside the driving/reading circuit 105.

The antenna electrode 2a, the gate electrode 2d, the reset line 2b, the storage capacitor electrode 2c, and the connection line 22 are integrally formed in the first conductive layer such that the antenna 41, the gate of the sensor TFT 30, the reset line 2b, the connection line 22, and the storage capacitor 43 are connected to each other. In contrast, the driving/reading circuit 105, the gate driver 103, and the source driver 104 each are not formed directly on the substrate 1a, but are formed on a semiconductor chip. The semiconductor chip is then mounted on the substrate 1a.

Figure 5:
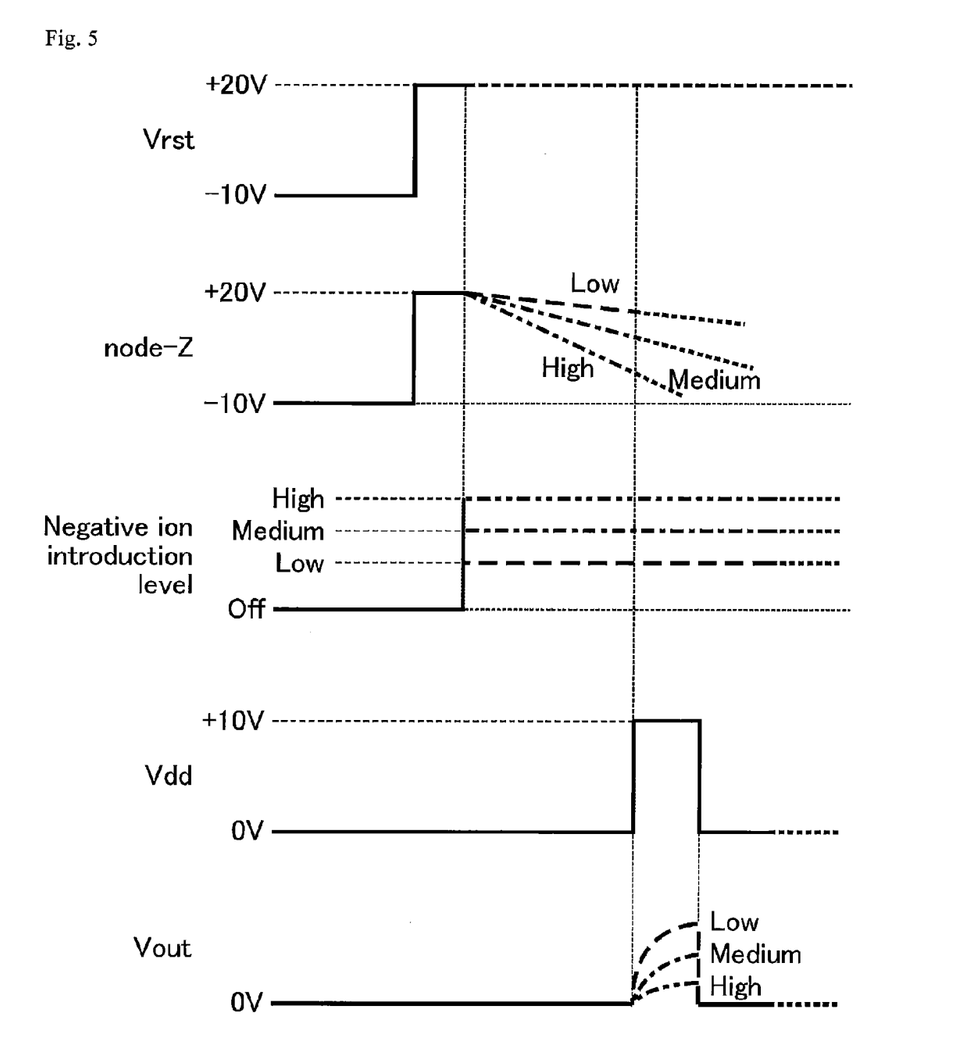
FIG. 5 is a timing chart of an ion sensor circuit according to Embodiment 1.

Next, the operational mechanism of the ion sensor circuit is described in detail using FIG. 5. FIG. 5 is a timing chart of the ion sensor circuit according to the present embodiment.

In the initial state, Vrst is set to a low voltage (−10 V). At this time, a power supply for applying a low voltage (−10 V) to the gate electrode 2e of the pixel TFT 40 can also be used as a power supply for setting Vrst to the low voltage (−10 V). Further, in the initial state Vdd is set to a low voltage (0 V). Before starting measurement of an ion concentration, first, a high voltage (+20 V) is applied to the reset line 2b and the voltage of the antenna 41 (voltage of the node-Z) is reset to +20 V. At this time, a power supply for applying a high voltage (+20 V) to the gate electrode 2e of the pixel TFT 40 can also be used as a power supply for applying Vrst. After the voltage of the node-Z has been reset, the reset line 2b is held in a high impedance state. Subsequently, when introduction of ions starts and negative ions are captured by the antenna 41, the voltage of the node-Z that has been reset to +20 V, that is, charged to a positive voltage, is neutralized by the negative ions and decreases (sensing operation). The higher the negative ion concentration is, the faster the speed at which the voltage decreases. After a predetermined time period has elapsed since introduction of ions began, a high voltage (+10 V) is temporarily applied to the input line 20. That is, a pulse voltage of +10 V is applied to the input line 20. In addition, the output line 21 is connected to the constant current circuit 25. Accordingly, when a pulse voltage of +10 V is applied to the input line 20, a constant current flows in the input line 20 and the output line 21. However, a voltage Vout of the output line 21 varies in accordance with the degree of opening of the gate of the sensor TFT 30, that is, a difference in the voltage of the node-Z. By detecting the voltage Vout with the ADC 26, it is possible to detect the negative ion concentration. In this connection, it is also possible to adopt a configuration in which the constant current circuit 25 is not provided, and a negative ion concentration is detected by detecting a current Id of the output line 21 that varies in accordance with a difference in the voltage of the node-Z.

According to the present embodiment, a high voltage of Vdd is not particularly limited to +10 V, and the high voltage of Vdd may be the same as a high voltage applied to the reset line 2b, that is, the same as the high voltage of +20 V that is applied to the gate electrode 2e of the pixel TFT 40. Thus, a power supply for applying the high voltage to the gate electrode 2e of the pixel TFT 40 can also be used as a power supply for applying the high voltage of Vdd.

Embodiment 2

A display device according to Embodiment 2 has the same configuration as Embodiment 1 except for the following points. That is, although the display device according to Embodiment 1 includes an ion sensor that is capable of measuring a negative ion concentration in the atmosphere using the N-channel sensor TFT 30, the display device according to Embodiment 2 includes an ion sensor that is capable of measuring a positive ion concentration in the atmosphere using a P-channel sensor TFT 30.

More specifically, $p^+$ a-Si layers are formed instead of the $n^+$ a-Si layers 5a and 5b, and the $p^+$ a-Si layers are doped with a third group element such as boron (B). That is, according to the present embodiment, the sensor TFT 30 and the pixel TFT 40 are P-channel TFTs.

Figure 6:
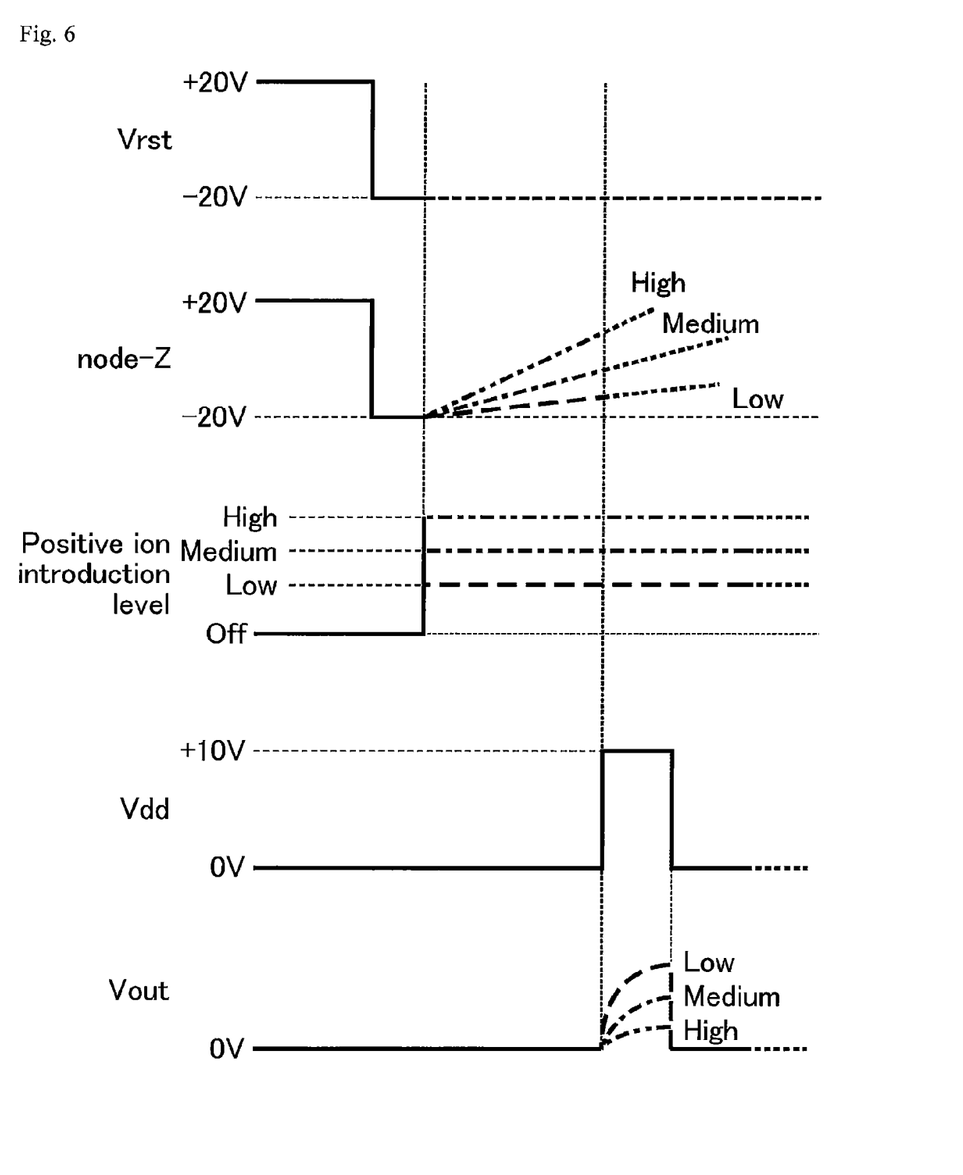
FIG. 6 is a timing chart of an ion sensor circuit according to Embodiment 2.

The operational mechanism of the ion sensor circuit will now be described in detail using FIG. 6. FIG. 6 is a timing chart of the ion sensor circuit according to the present embodiment.

In the initial state, Vrst is set to a high voltage (+20 V). At this time, a power supply for applying a high voltage (+20 V) to the gate electrode 2e of the pixel TFT 40 can also be used as a power supply for setting Vrst to the high voltage (+20 V). Further, in the initial state, Vdd is set to a low voltage (0 V). Before starting measurement of an ion concentration, first a low voltage (−20 V) is applied to the reset line 2b to reset the voltage of the antenna 41 (voltage of the node-Z) to −20 V. After the voltage of the node-Z has been reset, the reset line 2b is held in a high impedance state. Subsequently, when an operation to introduce ions is commenced and positive ions are captured by the antenna 41, the voltage of the node-Z that has been reset to −20 V, that is, charged to a negative voltage, is neutralized by the positive ions and increases (sensing operation). The higher the positive ion concentration is, the faster the speed at which the voltage increases. After a predetermined time period has elapsed since introduction of ions began, a high voltage (+10 V) is temporarily applied to the input line 20. That is, a pulse voltage of +10 V is applied to the input line 20. Further, the output line 21 is connected to the constant current circuit 25. Accordingly, when a pulse voltage of +10 V is applied to the input line 20, a constant current flows in the input line 20 and the output line 21. However, the voltage Vout of the output line 21 varies in accordance with the degree of opening of the gate of the sensor TFT 30, that is, a difference in the voltage of the node-Z. By detecting the voltage Vout with the ADC 26, it is possible to detect the positive ion concentration. In this connection, it is also possible to adopt a configuration in which the constant current circuit 25 is not provided, and in which the positive ion concentration can be detected by detecting a current Id of the output line 21 that varies in accordance with a difference in the voltage of the node-Z.

Further, according to the present embodiment, the low voltage that is applied to the reset line 2b is not particularly limited to −20 V, and the low voltage may be −10 V that is the same as the low voltage applied to the gate electrode 2e of the pixel TFT 40. Thus, a power supply for applying a low voltage to the gate electrode 2e of the pixel TFT 40 can used be also as a power supply for applying a low voltage to be applied to the reset line 2b. In addition, the high voltage of Vdd is not particularly limited to +10 V, and the high voltage may be the same as the high voltage applied to the reset line 2b, that is, the same as the high voltage of +20 V applied to the gate electrode 2e of the pixel TFT 40. Thus, a power supply for applying a high voltage to the gate electrode 2e of the pixel TFT 40 can also be used as a power supply for applying the high voltage of Vdd.

Hereinafter, modification examples of Embodiments 1 and 2 are described.

Although Embodiments 1 and 2 have been described using a liquid crystal display device as an example, a display device of each embodiment may also be an FPD such as a plasma display or an organic EL display.

The constant current circuit 25 may not be provided. That is, the ion concentration may be calculated by measuring the current between the source and drain of the sensor TFT 30.

The conduction type of the TFTs formed in the ion sensor portion 120 and the conduction type of the TFTs formed in the display 130 may be different from each other.

A μc-Si layer, p-Si layer, CG-Si layer, or an oxide semiconductor layer may be used instead of the hydrogenated a-Si layer. Since μc-Si is highly sensitive to light as a-Si is, TFTs including a μc-Si layer are preferably shielded from light. In contrast, p-Si, CG-Si, and an oxide semiconductor have a low sensitivity to light, and thus TFTs including a p-Si layer or CG-Si layer may not be shielded from light.

The kind of the semiconductor for TFTs formed in the ion sensor portion 120 and the kind of the semiconductor for TFTs formed in the display 130 may be different from each other, but are preferably the same as each other, for simplification of the production process.

The TFTs formed on the substrate 1a are not limited to bottom-gate TFTs, and may be top-gate TFTs or planer TFTs. For example, when the sensor TFT 30 is of a planer type, the antenna 41 may be formed over the channel region of the TFT 30. That is, the gate electrode 2d may be exposed and the gate electrode 2d itself may be configured to function as an ion sensor antenna.

The TFTs formed in the ion sensor portion 120 and the TFTs formed in the display 130 may be different from each other.

The gate driver 103, the source driver 104, and the driving/reading circuit 105 may be monolithic, and directly formed on the substrate 1a.

The above embodiments may be appropriately combined with each other without departing from the scope of the present invention.

Example 1

Display Device

A liquid crystal display device including an ion sensor for which a detection object is negative ions in air was prepared in the same manner as Embodiment 1. More specifically, the sensor TFT 30 was an N-channel TFT of the bottom-gate type formed from hydrogenated a-Si that was configured so that the channel length (L)/channel width (W)=4 μm/60 μm. The area of the antenna 41 was 400 μm×400 μm. A capacitor with a capacitance of 1 pF was used as the node-Z storage capacitor 43.
(Driving Conditions)

Voltages of 0 V and +10 V were adopted as the low voltage and high voltage of Vdd, respectively. Voltages of −10 V and +20 V were adopted as the low voltage and high voltage of Vrst, respectively.
(Ion Generator)

The Plasmacluster Ion Generator IG-820-W manufactured by Sharp Corporation was used as an ion generator. The term "plasmacluster ions" refers to ions that are generated by applying positive and negative voltages to discharge electrodes to electrolyze airborne water molecules and oxygen molecules to thereby generate positive ions ($H^+$) and negative ions ($O^-$), and allowing water molecules to gather around the positive ions ($H^+$) and negative ions ($O^-$) to stabilize the ions.
(Measurement Details)

Variations with time in a current Id flowing through the output line and a voltage of the node-Z were measured under a temperature condition of 27° C. with respect to four kinds of air, namely, dry air, air with a low plasmacluster ion concentration ($700\times10^3$ ions/cm$^3$), air with a medium plasmacluster ion concentration ($1500\times10^3$ ions/cm$^3$), and air with a high plasmacluster ion concentration ($2000\times10^3$ ions/cm$^3$).

Figure 7:
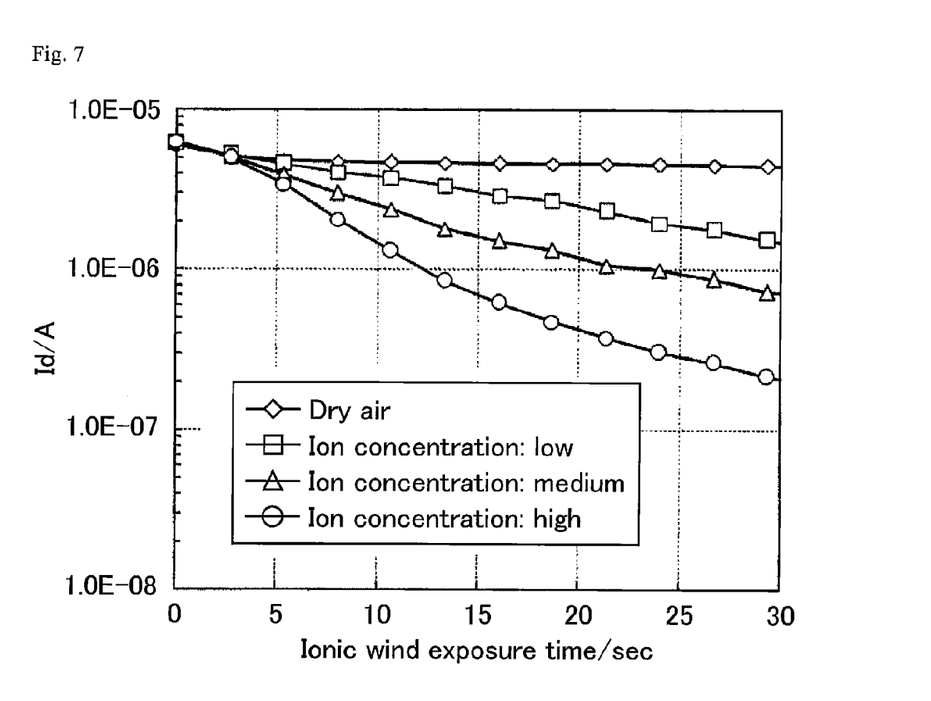
FIG. 7 is a graph that shows variations with time in Id values with respect to four kinds of air according to Example 1.

The variations with time in the Id values for the four kinds of air are shown in FIG. 7. A difference between the Id value for the high negative ion concentration and the Id value for the low negative ion concentration at 8 seconds after the start of measurement was approximately 1.5 μA.

Figure 8:
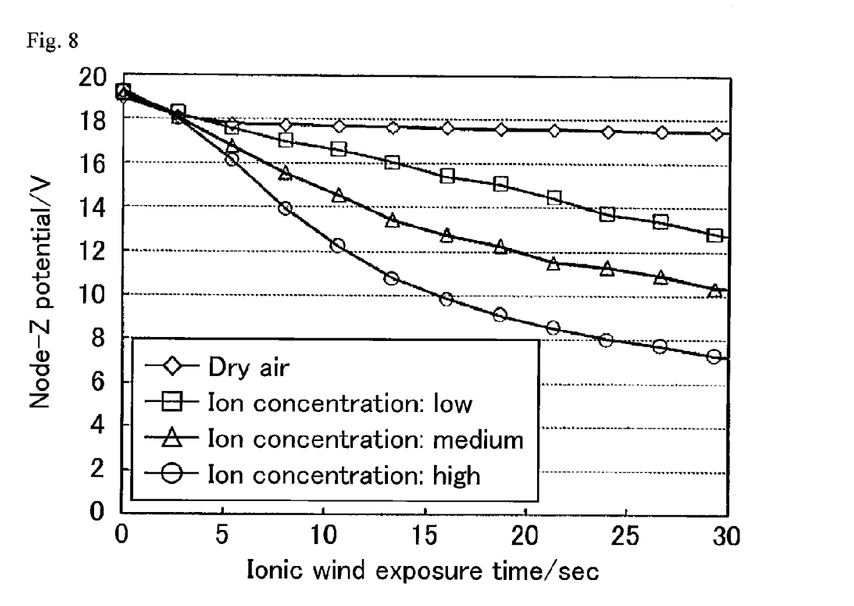
FIG. 8 is a graph that shows variations with time in a node-Z potential with respect to four kinds of air according to Example 1.

Variations with time in the voltage of the node-Z for the four kinds of air are shown in FIG. 8. As described in the foregoing, the higher that the negative ion concentration was, the greater the degree to which the voltage of the node-Z decreased. A difference between the voltage of the node-Z in the case of the high negative ion concentration and the voltage of the node-Z in the case of the low negative ion concentration at 8 seconds after the start of measurement was approximately 2 V.

As described above, it was established that it is possible to favorably measure a negative ion concentration in the atmosphere by means of the display device including the ion sensor according to the present example.

Further, the area occupied by the ion sensor circuit 107 of Example 1 was on the order of micrometers, and thus the ion sensor circuit 107 of Example 1 was sufficiently small in comparison to the ion sensor portion provided in the conventional ion generating apparatus that is described above.

Note that the ion sensor portion provided in the conventional ion generating apparatus performs from the role of an antenna portion to output of a sensor signal, and which exerts approximately the same functions as the ion sensor circuit 107 formed on the substrate 1a.

The present application claims priority to Patent Application No. 2010-128166 filed in Japan on Jun. 3, 2010 under the Paris Convention and provisions of national law in a designated State, the entire contents of which are hereby incorporated by reference.

REFERENCE SIGNS LIST 1a, 1b: Insulating substrate
2a: Ion sensor antenna electrode
2b: Reset line
2c, 8: Node-Z storage capacitor electrode
2d, 2e: Gate electrode
3: Insulating film
4a, 4b: Hydrogenated a-Si layer
5a, 5b: $n^+$ a-Si layer
6a, 6b: Source electrode
7a, 7b: Drain electrode
9: Passivation film
10a, 10b: Contact hole
11a: Transparent conductive film (first transparent conductive film)
11b: Transparent conductive film (second transparent conductive film)
12a: Light-shielding film (first light-shielding film)
12b: Light-shielding film (second light-shielding film)
13: Color filter
20: Input line
21: Output line
22: Connection line
25: Constant current circuit
26: Analog-digital conversion circuit (ADC)
30: Sensor TFT (first FET)
31a, 31b: Polarizer
32: Liquid crystal
36: Liquid crystal storage capacitor (Cs)
40: Pixel TFT (second FET)
41: Ion sensor antenna
42: Air ion lead-in/lead-out path
43: Node-Z storage capacitor
101: Display-driving TFT array
103: Gate driver (display scanning signal line-driving circuit)
104: Source driver (display image signal line-driving circuit)
105: Ion sensor driving/reading circuit
106: Arithmetic processing LSI
107: Ion sensor circuit
109: Power supply circuit
110: Display device
115: Display-driving circuit
120, 125: Ion sensor portion
130, 135: Display

The invention claimed is:

1. A display device comprising:
an ion sensor portion including an ion sensor circuit;
a display including a display-driving circuit; and
a substrate, wherein
at least one portion of the ion sensor circuit and at least one portion of the display-driving circuit are formed on the same main surface of the substrate,
the ion sensor circuit includes a first field effect transistor and an ion sensor antenna,
the ion sensor antenna is connected to a gate electrode of the first field effect transistor;
the display-driving circuit includes a second field effect transistor, and
the first field effect transistor, the ion sensor antenna and the second field effect transistor are located on the same main surface of the substrate.

2. The display device according to claim 1,
wherein the ion sensor antenna includes a surface that includes a transparent conductive film.

3. The display device according to claim 2,
wherein
the transparent conductive film is a first transparent conductive film, and
the display includes a second transparent conductive film.

4. The display device according to claim 3,
wherein the first transparent conductive film and the second transparent conductive film include the same material(s).

5. The display device according to claim 1,
wherein
the first field effect transistor includes a semiconductor whose properties are changed by light, and
the semiconductor is shielded from light by a light-shielding film.

6. The display device according to claim 5,
wherein:
the light-shielding film is a first light-shielding film; and
the display includes a second light-shielding film.

7. The display device according to claim 6,
wherein the first light-shielding film and the second light-shielding film include the same material(s).

8. The display device according to claim 1,
wherein the ion sensor antenna does not overlap with a channel region of the first field effect transistor.

9. The display device according to claim 1,
wherein the first field effect transistor includes amorphous silicon or microcrystalline silicon.

* * * * *